(12) United States Patent
Fresquet et al.

(10) Patent No.: US 9,494,529 B1
(45) Date of Patent: Nov. 15, 2016

(54) CHROMATIC CONFOCAL DEVICE AND METHOD FOR 2D/3D INSPECTION OF AN OBJECT SUCH AS A WAFER WITH VARIABLE SPATIAL RESOLUTION

(71) Applicant: FOGALE NANOTECH, Nîmes (FR)

(72) Inventors: Gilles Fresquet, Garrigues-Sainte-Eulalie (FR); Alain Courteville, Congénies (FR); Philippe Gastaldo, Pontcharre (FR)

(73) Assignee: FOGALE NANOTECH, Nîmes (FR)

( * ) Notice: Subject to any disclaimer, the term of this patent is extended or adjusted under 35 U.S.C. 154(b) by 0 days.

(21) Appl. No.: 15/184,758

(22) Filed: Jun. 16, 2016

(30) Foreign Application Priority Data

Mar. 25, 2016 (EP) ..................... 16305349

(51) Int. Cl.
*G01N 21/00* (2006.01)
*G01N 21/88* (2006.01)
*G01N 21/95* (2006.01)

(52) U.S. Cl.
CPC ...... *G01N 21/8806* (2013.01); *G01N 21/9501* (2013.01); *G01N 2201/06* (2013.01)

(58) Field of Classification Search
CPC ..................... G01N 21/9501; G01N 2201/06; G01N 21/8806
USPC ...................... 356/237.1–237.6, 239.1–239.8
See application file for complete search history.

(56) References Cited

U.S. PATENT DOCUMENTS

| | | | |
|---|---|---|---|
| 6,043,932 A | 3/2000 | Kusunose | |
| 6,934,019 B2 | 8/2005 | Geffen et al. | |
| 8,599,372 B2 * | 12/2013 | Chen | G02B 21/0032 356/300 |
| 2015/0260504 A1 | 9/2015 | Schoenleber et al. | |

FOREIGN PATENT DOCUMENTS

| | | |
|---|---|---|
| FR | 2950441 | 3/2011 |
| FR | 3006758 | 12/2014 |

OTHER PUBLICATIONS

European Search Report for European Patent Application No. EP 16305349.9 dated Jul. 4, 2016.

* cited by examiner

*Primary Examiner* — Tri T Ton
(74) *Attorney, Agent, or Firm* — Greer, Burns & Crain, Ltd.

(57) ABSTRACT

A confocal chromatic device is provided for inspecting the surface of an object such as a wafer, including a plurality of optical measurement channels with collection apertures arranged for collecting the light reflected by the object through a chromatic lens at a plurality of measurement points, and a magnifying lens arranged for introducing a variable or changeable scaling factor between the spatial repartition of the collection apertures and the measurement points. A method is also provided for inspecting the surface of an object such as a wafer including tridimensional structures.

18 Claims, 3 Drawing Sheets

CHROMATIC CONFOCAL DEVICE AND METHOD FOR 2D/3D INSPECTION OF AN OBJECT SUCH AS A WAFER WITH VARIABLE SPATIAL RESOLUTION

BACKGROUND

The invention relates to a device and method for inspecting an object such as a wafer, and more particularly for inspecting an object comprising structures such as bumps or micro-bumps.

The field of the invention is, but not limited to, 2D-3D inspection and metrology for semiconductor industry.

Chromatic confocal technique is a well-known technique for tridimensional (3D) surface mapping or profilometry, in particular for semiconductor applications.

The technique relies on the use of a chromatic lens with an enhanced chromatism, whose focal length depends strongly on the optical wavelength. Each wavelength of the light crossing such lens is focused at a different distance, or in a different focal plane.

The chromatic lens is embedded in a confocal set-up with source and detection pinholes (usually made by optical fibers) placed at the confocal planes of the chromatic lens to reject out-of-focus lens. When a reflecting surface is placed in front of the chromatic lens, only the light with the wavelength whose focal plane corresponds to the position of the surface is transmitted by the detection pinhole.

Detection is made by a spectrometer, which comprises usually a dispersing element and a linear sensor (linear CCD) to acquire the intensity spectrum of the light. The height (or distance) of the surface relative to the chromatic lens is obtained by analyzing the intensity spectrum of the detected light.

Such set-up allows measuring distances on a single point at the time. So inspecting a full wafer surface by scanning all the surface may be very time-consuming. Actually, the factor limiting the measurement speed is the readout time of the linear sensor for acquiring the intensity spectrum.

Acquisition speed can be improved by providing several measurement channels in parallel.

We know for instance the document US 2015/0260504 which discloses an implementation of a confocal chromatic device in which several measurement channels are provided through a chromatic lens with several optical fibers. The sensor allows measuring distance or height at several points on the surface of the object simultaneously.

However, even if the acquisition rate is improved, the time for inspecting a full wafer surface remains very long.

Another issue when measuring or inspecting patterned wafers is the accurate localization of the measurement points relative to the existing structures. That issue is usually solved by using a 2D (bidimensional) inspection or imaging system such as a camera.

We know for instance the document U.S. Pat. No. 6,934,019 which describes an inspection system based on a chromatic confocal sensor which comprises also an imaging camera. The measurements require two steps: first acquiring an image of the wafer with the camera and computing a map of the locations of the structures to be measured; and second performing the height measurements.

However, the switching between the camera and the chromatic sensor is time consuming and the need for mechanical displacements to position either the camera or the chromatic confocal sensor above the structures to be measured may impact the positioning accuracy for the height measurement.

It is an object of the invention to provide a device and a method allowing fast and accurate 2D (bidimensional or in-plane imaging) inspection of an object such as a wafer.

It is also an object of the invention to provide a device and a method allowing fast and accurate 3D (tridimensional height measurements) inspection of an object such as a wafer.

It is also an object of the invention to provide a device and a method allowing providing simultaneously or at least during a same scan and with minimized positioning uncertainty an intensity image (2D) and accurate height measurements (3D) on an object such as a wafer with patterns or structures.

It is also an object of the invention to provide a device and a method allowing accurate locating of height measurement positions, and/or accurate positioning of height measurement probes relative to structures or patterns on an object such as a wafer.

It is also an object of the invention to provide a device and a method allowing characterizing or inspecting structures (in 2D and/or in 3D) of an object such as a wafer in position and shape.

It is also an object of the invention to provide a device and a method allowing adjusting a spatial resolution and/or a spatial repartition of measurement points so as to match characteristics of inspected structures such as spatial periodicity, size and/or spacing.

It is also an object of the invention to provide a device and a method for inspecting bumps, trenches and other patterned structures on an object such as a wafer.

SUMMARY

Such objects are accomplished through a confocal chromatic device and a method for inspecting the surface of an object such as a wafer.

According to a first aspect of the invention, it is thus proposed a confocal chromatic device for inspecting the surface of an object such as a wafer, comprising:
  a chromatic lens with an extended axial chromatism;
  a light source for illuminating the object through the chromatic lens with a plurality of optical wavelengths being focused at different axial distances;
  a plurality of optical measurement channels with collection apertures arranged for collecting the light reflected by the object through the chromatic lens at a plurality of measurement points;
  Characterized in that it further comprises a magnifying lens arranged for introducing a variable or changeable scaling factor between the spatial repartition of the collection apertures and the measurement points.

The chromatic lens may comprise any kind of chromatic lens or lens assembly having a suitable chromatic aberration over a field of view, such as for instance:
  a single lens or lens assembly shared between the optical measurement channels;
  a plurality of lenses or microlenses each used by only one or several optical measurement channels;
  holographic elements;
  diffractive lens or microlens elements.

The chromatic lens may comprise at least a lens made with a dispersive material, and any other lenses required for providing the necessary optical arrangement. Such lens may be designed according to well-known techniques so as to provide a strong chromatic aberration, allowing different optical wavelengths crossing the lens to be focused at different distances, and that over a lateral field of view.

The confocal chromatic device of the invention thus comprises several optical measurement channels. Each optical measurement channel is sensitive to the light reflected at a specific measurement point in a plane perpendicular to the optical axis of the chromatic lens, and along a range of axial distances or heights (in a direction substantially parallel to the optical axis of the lens) corresponding to the planes of focalization of the different optical wavelengths crossing the chromatic lens. That range of axial distances allowing measurement may be defined as the measurement range of the device.

In other words, the measurement points correspond to the conjugate points of the collection apertures, or, more precisely, to the projection of the conjugate points of the collection apertures for the different wavelengths on a plane perpendicular to the optical axis of the chromatic lens. These collection apertures operate as pinholes allowing rejecting out-of-focus light, according to a classical confocal detection scheme.

The light source may comprise any kind of light source capable of emitting light at a plurality of wavelengths covering a spectral range for which the chromatism of the chromatic lens is efficiently usable. It may comprise for instance light-emitting diodes (LED), thermal light sources such as halogen lamps, or gas-discharge lamps. It may also comprise a tunable laser, a white laser or a supercontinuum photonic source. The light source may generate light with wavelengths within for instance a range of 400-700 nm (visible range) allowing inspection of surfaces and/or transparent layers in the visible range. Alternatively, the light source may generate light with wavelengths above 1 micron in the infrared range, allowing for instance inspections through layers of silicon or other materials transparent in the infrared.

The light source may comprise a single light source shared between all the optical measurement channels, or a plurality of light sources each shared between several optical measurement channels, or a light source per optical measurement channel.

According to some modes of realization of the invention, the plurality of optical measurement channels may comprise optical measurement channels with an intensity detector for measuring a total intensity of the collected light.

Intensity detectors may comprise any photodetector measuring an intensity of light, or a global intensity of light over a spectral range.

According to some modes of realization, intensity detectors may comprise:
  Separate or discrete intensity detectors for each optical measurement channel, such as for instance phototransistors, photodiodes or avalanche photodiodes; and/or
  Intensity detectors shared between a pluralities of optical measurement channel. Such intensity detectors may comprise for instance photodiode arrays, line or matrix CCD or CMOS in which intensity measurements of different optical measurement channels are done on different pixels.

The intensity detectors provide a global intensity of light at the measurement point. So they provide a 2D image information of the object.

The 2D measurements benefit from an extended depth of focus, because of the chromatic confocal set-up. The image which is obtained by these means is in focus or well-focused over the whole measurement range of the device, because it is done mostly using the wavelength focused on the surface of the object, whatever position that surface may have in the measurement range. So the available depth of focus for the imaging is determined by the extent of the chromatic aberration of the chromatic lens. It is thus much larger than the depth of focus which would be available with a classical achromatic lens, and which correspond to the depth of focus available for a single wavelength with the chromatic lens.

According to some modes of realization of the invention, the plurality optical of measurement channels may further comprise at least one optical measurement channel with a spectral detector for measuring a spectral information of the collected light and deducing an axial distance information.

Such spectral detector(s) may comprise any detector capable of providing an information relative to an intensity of light in function of optical wavelengths, such as for instance:
  Spectrometer type devices with a dispersing element such as a grating or a diffraction array and a sensor capable of collecting a light intensity for the different wavelengths, such as for instance a line CCD, CMOS or a photodiode array;
  Devices with color filters in front of a line or matrix detector, allowing a detection selective in wavelength with different detector areas.

Spectral detector may also comprise detectors shared between several optical measurement channels, such as line or matrix CCD or CMOS. In that case, intensity spectra of different optical measurement channels are collected on different areas or pixels of the detector.

The axial distance information may be deduced from the intensity spectrum by identifying the peak(s) in the spectrum or the wavelengths which are the most reflected, and which are representative of the location of the corresponding interfaces of an object in the measurement range. Of course, in presence of a transparent object with several detectable layers, several peaks representative of optical distances to several interfaces may be identified.

So, the spectral detectors provide an axial distance, or a height information at the measurement point. They thus provide a 3D information which is the usual purpose of the chromatic confocal sensors.

The invention thus allows doing a sensor with 2D and/or 3D inspection capabilities.

So, according to some modes of realization, the device of the invention may comprise:
  Only optical measurement channels with an intensity detector for measuring a total intensity of the collected light. In that case the device of the invention is devoted to fast 2D inspection (intensity imaging) with an extended depth of focus;
  Only optical measurement channels with a spectral detector for measuring an axial distance information. In that case the device of the invention is devoted to 3D inspection, which is the classical way of using chromatic confocal devices;
  Optical measurement channels with an intensity detector and optical measurement channels with a spectral detector, thus providing a sensor with 2D and 3D inspection capabilities in a single measurement head. The measurement points for the 2D and 3D inspection are then in a fixed, stable and well known spatial relationship.

2D total intensity measurement can be done much faster than 3D axial distance measurements, because their only limitation in terms of acquisition rate relate to the integration time or bandwidth of the detector. In the other hand, 3D axial measurement rates are limited at least by the integration time and readout time of spectrometer sensors. As consequence, 2D measurement may be done at acquisitions rates 10 times or even much faster than 3D measurements. For instance, 2D measurement may be done at acquisition rates of several tens of kilohertz (for instance 50 KHz to 100 KHz), whereas 3D measurements may be done only at acquisition rates of a few kilohertz.

So, the device of the invention is particularly well adapted for high speed inspection, because it allows for instance:
- fast 2D inspection with an extended depth of focus, allowing for instance inspection of the surface of an object with extended tridimensional structures (such as bumps, pillars, nails, . . . ) with an optimal lateral resolution at any measurement points without refocusing; and/or
- fast 2D inspection of the surface of a structured object, and on-the-flight 3D measurement at selected points of interest; and/or
- 3D inspection.

According to some modes of realization, the optical measurement channels may comprise optical waveguides, or planar optical waveguides.

According to some modes of realization, the optical measurement channels may comprise optical fibers.

According to some modes of realization, the broadband light source may be conveyed through illumination apertures arranged in a confocal configuration relative to the chromatic lens and the collection apertures.

The device of the invention may then comprise a beam splitter inserted between the chromatic lens and, respectively, the illumination apertures and the collection apertures. The beam splitter may be preferably inserted in a part where the propagating beams are collimated, for instance using collimating lenses. Or course, the collection apertures and the illumination apertures shall be arranged so that a collection aperture and an illumination aperture are both conjugate points of a same measurement point, through the beam splitter and the chromatic lens.

According to some modes of realization, the optical measurement channels may comprise illumination optical fibers, an end of which being used as illumination apertures.

These illumination optical fibers may comprise multimode, or single mode fibers. They may be arranged or grouped in bundles. They may have an end corresponding to the illumination apertures positioned in a mount piece with for instance v-grooves for accurate positioning.

According to some modes of realization, the device of the invention may comprise collection apertures comprising, for instance:
- pinholes, like through holes in a mask or a wall;
- an entrance slit, corresponding to a through aperture elongated on one direction, which materializes several collection apertures for several optical measurement channels arranged in line;
- pixels or detection elements of a detector.

According to some modes of realization, the optical measurement channels may comprise collection optical fibers, an end of which being used as collection apertures.

These collection fibers may comprise multimode, or single mode fibers. They may be arranged or grouped in bundles. They may have an end corresponding to the collection apertures positioned in a mount piece with for instance v-grooves for accurate positioning.

According to some modes of realization, the broadband light source may be conveyed by the collection optical fibers.

The optical measurement channels may then comprise a coupler or a fiber coupler for directing the light of the light source to the collection aperture, and directing the light collected back by the collection aperture towards a detector.

According to some modes of realization, the device of the invention may comprise at least one optical routing element allowing doing at least one of the following:
- Using an intensity detector and a spectral detector to do measurements simultaneously or sequentially on one optical measurement channel;
- Selectively using an intensity detector and/or a spectral detector with a plurality of optical measurement channels.

Such optical routing element may comprise for instance:
- A coupler for splitting the light collected on an optical measurement channel between an intensity detector and a spectral detector. In that case, total intensity and spectral information may be obtained on a same optical measurement channel in parallel (in a synchronous or asynchronous way), or sequentially;
- An optical switch for directing the light collected on an optical measurement channel towards either an intensity detector or a spectral detector. In that case, total intensity and spectral information may be obtained on a same optical measurement channel sequentially;
- An optical multiplexer, comprising for instance several optical switches, for selectively connecting intensity detector(s) and/or spectral detector(s) to several measurement channels, so as for instance to share such intensity detector(s) and/or spectral detector(s) between several optical measurement channels, or to select intensity detector(s) and/or spectral detector(s) to connect to one optical measurement channel.

According to some modes of realization, the device of the invention may comprise a magnifying lens positioned between the collection apertures and the chromatic lens.

As previously explained, such magnifying lens is arranged for introducing a variable or changeable scaling factor between the spatial repartition of the collection apertures and the measurement points.

The magnifying lens may comprise any kind of lens or lens assembly. It may be essentially achromatic for the used wavelengths (or achromatic for the wavelengths of the light source used in detectors).

The device may of course comprise other lenses placed between the collection apertures and the magnifying lens, and/or other lenses placed between the magnifying lens and the chromatic lens.

Several configurations are possible.

According to some modes of realization, the device of the invention may comprise a magnifying lens and a chromatic lens arranged so that to provide an intermediate conjugate focal plane which is simultaneously:
- A conjugate focal plane of the plane with the collection apertures for a lens assembly comprising the magnifying lens; and
- A conjugate focal plane of the plane with the measurement points for a lens assembly comprising the chromatic lens.

According to some modes of realization, the intermediate conjugate focal plane may be:
- At a finite distance; or
- At a finite distance and positioned between the magnifying lens and the chromatic lens.

It may then form a real image plane of the collection apertures.

According to some modes of realization, the intermediate conjugate focal plane may be at infinite distance, corresponding to collimated beams.

According to some modes of realization, the device of the invention may comprise a collimating lens positioned between the collection apertures and the magnifying lens.

Such collimating lens may for instance be uses with a beam splitter as previously explained. It may be arranged with the collection apertures positioned in its focal plane, so as to provide to the magnifying lens collimated beams.

The device of the invention may then comprise a magnifying lens with an afocal lens arrangement.

Such afocal lens arrangement has an infinite effective focal length. It may be done for instance with two converging lenses positioned so that their spacing corresponds to the sum of their focal lengths (or their intermediate focal planes are at the same position).

In all cases, the plane with the measurement points is an image plane (or a conjugate plane) of the plane with the collection apertures by the whole optical assembly comprising the magnifying lens and the chromatic lens. Or in other words the measurement points are respective images of the collection apertures by that whole optical assembly. Such images are formed with a lateral magnification factor which depend on the magnification lens (for a given or particular chromatic lens of course). So, changing the magnification factor provided by the magnifying lens allows changing the spatial repartition of the measurement points by a scaling factor without changing the chromatic lens.

Of course, the scaling factor or the magnification factor may correspond to a magnification (absolute value higher than one), a reduction (absolute value lower than one) or a unity magnification (absolute value equal to 1).

The use of the magnifying lens allows changing the spatial repartition of the measurement points, continuously and/or by discrete steps, without changing the chromatic lens and thus without changing significantly the measurement range defined by the chromatic dispersion of that chromatic lens.

In addition, by taking care of providing magnifying lenses arrangements which allow positioning the intermediate conjugate focal plane at the same position along the optical axis relative to the chromatic lens (or at infinity), the chromatic lens is always used in similar conditions.

According to some modes of realization, the device of the invention may comprise a magnifying lens of a zoom type allowing introducing a variable magnification.

The magnifying lens may comprise for instance a zoom lens, or a magnifying lens or lens assembly of a zoom type.

Such magnifying lens (of a zoom type) may comprise:
  At least one lens movable (along the optical axis) and allowing varying a magnification;
  A lens arrangement allowing varying the magnification between the plane of the collection apertures and an intermediate conjugate focal plane at finite distance;
  An afocal zoom arrangement allowing modifying the width of collimated beams, for operating with an intermediate conjugate focal plane at infinite distance.

The device of the invention may further comprise a mechanical mount allowing changing a magnifying lens.

The mechanical mount may comprise for instance a turret or a linear stage.

It may allow combining several magnifying lenses with different magnification with one chromatic lens. For instance, it may hold several magnifying lenses on a moving stage (such as a turret or a linear stage) so as to be able to position any of them between the collection apertures and the chromatic lens.

Of course, the mechanical mount may allow changing magnifying lenses, at least some of which being magnifying lens of a zoom type.

The device of the invention may further comprise a mechanical mount allowing changing a combination of magnifying lens and chromatic lens, such as:
  Several magnifying lenses with several chromatic lens;
  One magnifying lens with several chromatic lenses.

According to some modes of realization, the device of the invention may comprise collection apertures arranged along a line.

Such configuration allows collecting light on measurement points also arranged along a line. These measurement points (and thus the collection apertures) may be equally spaced.

Such configuration allows doing measurement of total intensity (2D) and/or of spectral information (3D) over a surface of the object by moving relatively the object and the chromatic lens in a direction perpendicular to the line of collection apertures.

According to some modes of realization, the device of the invention may further comprise collection apertures respectively arranged along a first line and a second line substantially parallel to the first line, the first line comprising collection apertures of optical measurement channels with an intensity detector, the second line comprising collection apertures of optical measurement channels with a spectral detector.

Such configuration allows for instance acquiring 3D spectral information with optical measurement channels of the second line on measurement points of interest selected using 2D total intensity information acquitted at higher rate using optical measurement channels of the first line, during a monotonous relative displacement of the object relative to the chromatic lens.

According to some modes of realization, the device of the invention may further comprise mechanical displacement stages for moving relatively the object and the chromatic lens.

The mechanical displacement stages may comprise translation plates and/or rotation plates.

According to another aspect of the invention, it is proposed a method for inspecting the surface of an object such as a wafer comprising tridimensional structures, comprising:
  providing a chromatic lens with an extended axial chromatism;
  illuminating the object through the chromatic lens with a plurality of optical wavelengths being focused at different axial distances;
  collecting the light reflected by the object through the chromatic lens at a plurality of measurement points using a plurality of optical measurement channels with collection apertures;
  The method further comprising changing optically a scaling factor between a spatial repartition of the collection apertures and a spatial repartition of the measurement points.

The scaling factor may correspond to a magnification. It may be changed using a magnifying lens.

According to some modes of implementation, the method of the invention may further comprise at least one of the following steps:
  measuring a total intensity of the light collected by at least one of the optical measurement channels for obtaining an intensity information;
  measuring a spectral information of the light collected by at least one of the optical measurements channels for obtaining an axial distance information.

The method of the invention may be implemented using a confocal chromatic device of the invention as previously described, or using any other confocal chromatic device allowing performing the method steps.

According to some modes of implementation, the method of the invention may further comprise at least one of the following steps:
- Adjusting a spatial repartition of the measurement points taking into account a spatial repartition of structures on the object;
- Adjusting a spacing of measurements points so as to substantially match a spacing of structures on the object.

The spacing of the structures may for instance be a center-to-center spacing, or a side-to side spacing.

The method of the invention may further comprise a step of:
- Obtaining an information on the spacing of the structures using a-priori knowledge on the object, or a description information of the object;
- Obtaining an information on the spacing of the structures using intensity information and/or axial distance information previously obtained.

According to some modes of implementation, the method of the invention may further comprise steps of:
- building an intensity image by combining intensity information obtained in a region of interest of the object; and/or
- building a height map by combining axial distance information obtained in a region of interest of the object.

According to some modes of implementation, the method of the invention may further comprise a step of comparing obtained axial distance information with reference value(s).

According to some modes of implementation, the method of the invention may be implemented for inspecting bump structures on a wafer.

Bump structure may comprise for instance bumps, microbumps, solder bumps, copper pilar, copper nails, Random Dielectric Layers (RDL), metal patterns . . . .

The method may comprise steps of:
- locating at least one bump structure on the surface of the object using intensity information;
- locating at least one point of interest corresponding to the summit of the bump structure;
- obtaining axial distance information at said at least one point of interest, and deducing a height information of said bump structure.

BRIEF DESCRIPTION OF THE DRAWINGS

The methods according to embodiments of the present invention may be better understood with reference to the drawings, which are given for illustrative purposes only and are not meant to be limiting. Other aspects, goals and advantages of the invention shall be apparent from the descriptions given hereunder.

DETAILED DESCRIPTION

It is well understood that the embodiments described hereinafter are in no way limitative. Variants of the invention can in particular be envisaged comprising only a selection of the features described below in isolation from the other described features, if this selection of features is sufficient to confer a technical advantage or to differentiate the invention with respect to the state of the prior art. This selection comprises at least one preferred functional feature without structural details, or with only one part of the structural details if this part alone is sufficient to confer a technical advantage or to differentiate the invention with respect to the state of the prior art.

In particular, all the described variants and embodiments can be combined if there is no objection to this combination from a technical point of view.

In the figures, the elements common to several figures retain the same references.

Figure 1:
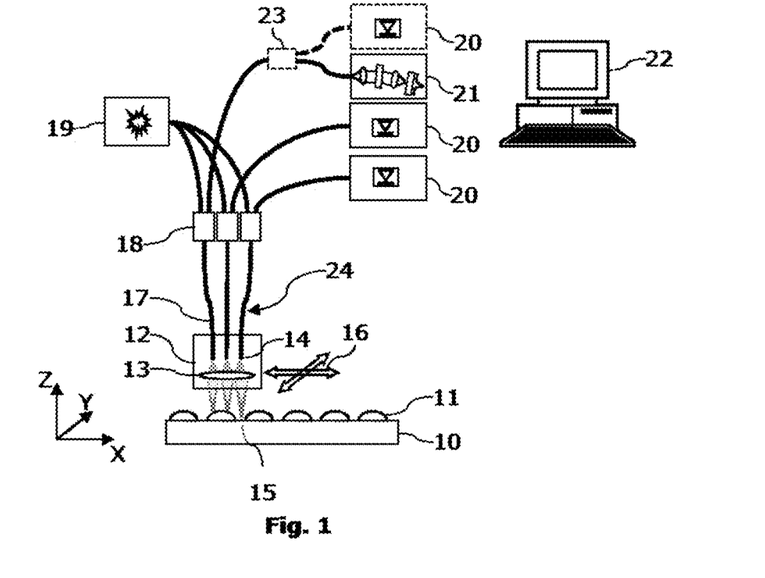
FIG. 1 illustrates a first mode of realization of confocal chromatic device of the invention.
Figure 2:
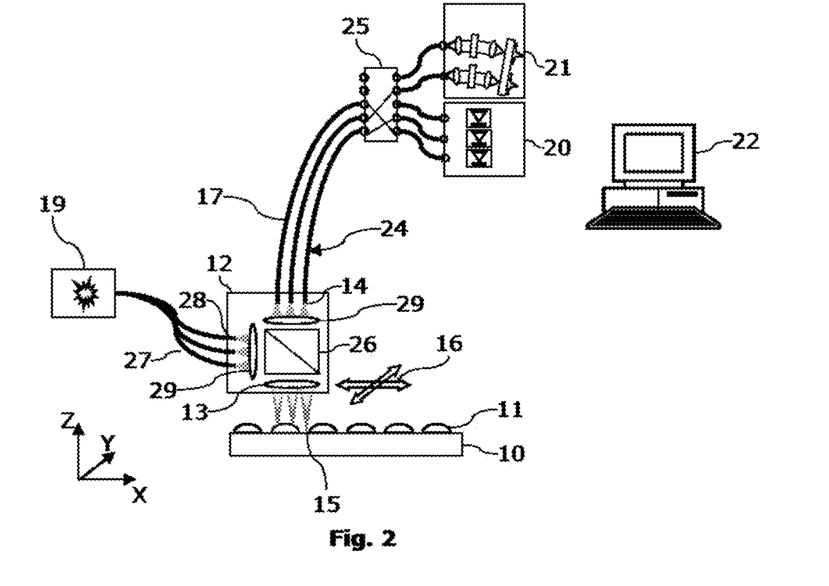
FIG. 2 illustrates a second mode of realization of confocal chromatic device of the invention.

With reference to FIG. 1 and FIG. 2, we will describe a confocal chromatic device of the invention. FIG. 1 and FIG. 2 illustrates several variant of implementation of some subparts of the device, which may of course be combined.

The confocal chromatic device comprises a measurement head 12 with a chromatic lens 13. Such lens is designed according to well-known techniques so as to provide a strong chromatic aberration, allowing different optical wavelengths crossing the lens to be focused at different axial distances (that is distances along the optical axis of the lens, or along the Z axis as shown in FIG. 1 and FIG. 2).

Of course, the chromatic lens 13 may comprise a single lens as illustrated in FIG. 1 and FIG. 2, or an arrangement of several individual lenses forming a chromatic lens assembly according to well-known techniques.

The confocal chromatic device further comprises several optical measurement channels 24.

Each optical measurement channel 24 comprises a collection optical fiber 17 for conveying the light to and from the measurement head 12 and the chromatic lens 13. In the mode of realization presented, these collection optical fibers 17 comprise multimode fibers arranged as a bundle. The collection fibers 17 have an end 14 positioned in the measurement head 12, which constitutes a collection aperture 14 of the confocal detection set-up. These collection apertures 14 are located in a collection plane (corresponding to an X-Y plane in FIG. 1 and FIG. 2) relative to the chromatic lens 13.

Each optical measurement channel 24 allows doing measurements on a measurement point 15 located in an object plane (corresponding to an X-Y plane) which is a conjugate plane of the collection plane for the chromatic lens 13. So, the measurement points 15 correspond to images of the collection apertures 14 by the chromatic lens 13, or, more precisely and because of the chromatic dispersion, projections of the images of the collection apertures 14 for the various wavelengths in the object plane. So the spatial repartition of the measurement points 15 in the object plane is determined by the spatial arrangement of the collection apertures 14 in the collection plane.

The optical measurement channels 24 are illuminated by a broadband light source 19. In the modes of realization presented, that light source 19 may comprise a thermal source (halogen for instance) or a LED source generating light with wavelengths within for instance a range of 400-700 nm (visible range).

In the mode of realization illustrated in FIG. 1, the light of the light source 19 is injected in optical fibers and conveyed through optical couplers 18 to the collection apertures 14. The couplers 18 may comprise fiber couplers, or couplers made with other technologies such as for instance planar optics waveguides. They may be done with distinct components for each optical measurement channel 24, or, in particular when using planar waveguide technologies, with components comprising several couplers 18 for several measurement channels 24.

In the mode of realization illustrated in FIG. 2, the light of the light source is conveyed by illumination optical fibers 27 to the measurement head 12. The measurement head 12 comprises a beam splitter 26 such as a beam splitter cube which directs the light issued from the illumination optical fibers 27 through their illumination aperture 28 (their end) towards the chromatic lens 13, and which allows coupling the light reflected back by the object 10 to the collection apertures 14 of the collection optical fibers 17. Two collimating lenses 29 are respectively arranged in front of the illumination apertures 28 and the collection apertures 14 to ensure that the beams crossing the beam splitter 26 are essentially collimated. Of course the chromatic lens 13 is arranged accordingly.

The illumination apertures 28 and the collection apertures 14 are spatially arranged so as to form respectively pairs of conjugate points with a measurement point 15. For that, two similar collimating lenses 29 are used and a same spatial repartition is done for the illumination apertures 28 and the collection apertures 14.

The light of the light source 19 is focuses by the chromatic lens 13 so that different wavelengths are focused at different axial positions on the measurement points 15, thus defining a measurement range.

The light reflected at the measurement points 15 by an object of interest 10 positioned in the measurement range is coupled back in the collection apertures 14. Thanks to the confocal arrangement of the set-up, only the light actually focused on an interface of the object 10 is coupled back in the collection apertures 14, and the light reflected by the object 10 out-of-focus is not coupled back. In addition, thanks to the chromatic dispersion of the chromatic lens 13:

The light focused on an interface (or a surface) of the object 10 correspond essentially to a single wavelength or group of wavelength for which the focal length of the chromatic lens 13 corresponds to the axial optical distance to that interface along the optical axis of the lens (corresponding to the Z axis). So by analyzing the intensity spectrum of the reflected light, the axial distance to the interfaces may be measured. That measurement mode, which corresponds to a classical use of the chromatic confocal technique, may be called profilometry mode or 3D detection mode;

The light collected after reflection on an interface (or a surface) of an object 10 located anywhere within the measurement range does not include any significant defocused light but only light focuses on that interface or surface. So it provides an intensity information with a lateral resolution in the object plane (X-Y) corresponding to the spot size at focus. And such lateral resolution is achieved for interfaces or surfaces located within the whole measuring range. So, by analyzing the total intensity of the reflected light, the set-up allows imaging interfaces or surfaces of the object 10 with a high lateral resolution over an extended depth of focus. This measurement mode has thus the advantage of allowing intensity imaging of surfaces of structures 11 of a significant height (as shown in FIG. 1 or FIG. 2) with an optimal lateral resolution in a 2D (bidimensional) detection mode.

According to some modes of realization, the device of the invention comprises only optical measurement channels 24 with an intensity detector 20 for measuring a total intensity of the collected light. In that case the device of the invention is devoted to fast 2D inspection (intensity imaging) with an extended depth of focus.

According to some modes of realization, the device of the invention comprises only optical measurement channels 24 with a spectral detector 21 for measuring an axial distance information. In that case the device of the invention is devoted to 3D inspection.

According to some modes of realization, the device of the invention comprises optical measurement channels 24 with (or coupled with) an intensity detector 20 and/or a spectral detector 21 for respectively acquiring data in 2D detection mode (intensity imaging) and/or 3D detection mode (profilometry).

In both cases, the light coupled back in the collection apertures 14 is transferred to these intensity detectors 20 and/or spectral detectors 21 by the collection optical fibers 17 and, in the mode of realization of FIG. 1, by the couplers 18.

Several arrangements of intensity detectors 20 and spectral detectors 21 within or in relation with the optical measurement channels 24 are possible. The device of the invention may notably comprise:

Optical measurement channels 24 which comprise only an intensity detector 20 or a spectral detector 21. In that case, these optical measurement channels 24 are dedicated to an intensity (2D) measurement or an axial distance (3D) measurement at the corresponding measurement point 15;

Optical measurement channels 24 which comprise an intensity detector 20 and a spectral detector 21. These optical measurement channels 24 further comprise a branching element 23 such as a coupler 23 or a switch 23 as illustrated in FIG. 1, for directing the light coupled back in the collection apertures 14 simultaneously or sequentially towards the intensity detector 20 and the spectral detector 21. In that case, these optical measurement channels 24 allow doing intensity measurements (2D) and axial distance measurements (3D) at the corresponding measurement point 15;

An optical multiplexer 25 with for instance an array of optical switches 25 as illustrated in FIG. 2 operating as in interconnection array and allowing interconnecting a plurality of optical measurement channels 24 with a plurality of intensity detectors 20 and/or spectral detectors 21 in a reconfigurable way. In that case, these optical measurement channels 24 may be configured on demand for doing an intensity (2D) measurement and/or an axial distance (3D) measurement at the corresponding measurement point 15.

The spectral detectors 21 as illustrated in the modes of realization of FIG. 1 and FIG. 2 comprise:

An entrance pupil, corresponding for instance to an end of a collection optical fiber 17, and a first lens for collimating the incoming light issued from the entrance pupil;

A dispersing element such as a diffraction array or a grating for dispersing angularly the different wavelengths of the incoming light;

A second lens and a linear detector such as a line CDD for re-imaging the dispersed light so that different wavelengths are focused on different pixels of the sensor. The intensity spectrum of the light is obtained by collecting the information on the pixels of the sensor. An interface of the object 10 present in the measurement range gives rise to a peak in the intensity spectrum around the wavelength focused at the corresponding axial position. So the intensity spectrum is analyzed to obtain an axial distance information, or the position of the interfaces or the surface of the object 10 within the measurement range.

The spectral detectors 21 of the different measurement channels 24 mays be completely distinct, or, as illustrated in FIG. 2, they may share some elements such as the detector. For instance, several spectral detectors 21 may share a same line or matrix sensor, the information of each spectral detector 21 being collected on a separate set of pixels of the shared detector. In the same way, several spectral detectors 21 may share a same dispersing element.

The intensity detectors 20 comprise point detectors such as photodiodes which measure the whole intensity of the light over the full spectrum.

The intensity detectors 20 of the different measurement channels 24 mays be distinct (using for instance individual photodiodes), or, as illustrated in FIG. 2, they may share some elements such as the detector. For instance, several intensity detectors 20 may share a same photodiode array, or a same line or matrix sensor (CCD or CMOS), the information of each intensity detectors 20 being collected on a separate pixel, set of pixel or photodiode.

In a variant of the mode of realization of FIG. 2, the collection apertures 14 may be arranged directly at the level of the intensity detectors 20 or the spectral detectors 21. In that case the measurement channels 24 comprise no collection optical fibers 17 and of course no optical multiplexer 25. For instance, the device of the invention may comprise:

Intensity detectors 20 positioned with the sensing element or sensing surface of their detector located in the collection plane with the collection apertures 14, which is a conjugate focal plane of the object plane with the measurement points 15. The collection apertures 14 are then materialized directly by the limited size of the sensing element (for instance when using a photodiode) or by the limited size of the pixels when using for instance a line or matrix CCD;

Intensity detectors 20 positioned with the sensing element or sensing surface of their detector located behind a pinhole mask or an entrance slit materializing the collection apertures 14 and positioned in the collection plane. An entrance slit may be used to materialize a series of collection apertures 14 arranged in line, facing for instance a line or matrix sensor shared between several intensity detectors 20;

Spectral detectors 21 positioned with their entrance pupil corresponding to the collection apertures 14 positioned in the collection plane. These entrance pupils may be shaped as pinholes. They may also correspond to an entrance slit materializing the entrance pupils of a series of spectral detectors 21 sharing for instance a same dispersing element and a matrix detector.

The device of the invention further comprises a computer or a microcontroller 22 for control and data processing.

For allowing inspection of an object 10 such as a wafer, the device of the invention further comprises a holder for holding the object 10 (for instance a wafer chuck) and a mechanical displacement stage 16 for moving relatively the measurement head 12 and the object 10. In the mode of realization presented, the mechanical displacement stage 16 may comprise translation plates for linear displacements along the X, Y, and Z axis, and a rotation stage for rotating the object 10 (the wafer) in the X-Y plane.

Of course the measurement head 12 may be distinct from the parts of the device holding the light source 19 and the detectors 20, 21, or the whole system, including the measurement head 12, may be done as a single assembly.

With reference to FIG. 3-FIG. 6, we will now describe some modes of realization of device of the invention allowing adjusting or varying the spatial separation of the measurement points 15 without mechanically moving the collection apertures 14.

Such mode of realization may be advantageous for instance for inspecting an object 10 with periodic structures 11. By adjusting the spatial separation of the measurement points 15 to matches the period of the structures 11, parallel 2D and/or 3D inspection of these structures 11 at optimal speed may be performed.

According to these mode of realization, the measurement head 12 further comprise a magnifying lens 31 or a magnifying lens assembly 31 inserted between the collection apertures 14 and the chromatic lens 13. The magnifying lens 31 is preferably an achromatic lens arrangement.

Figure 3:
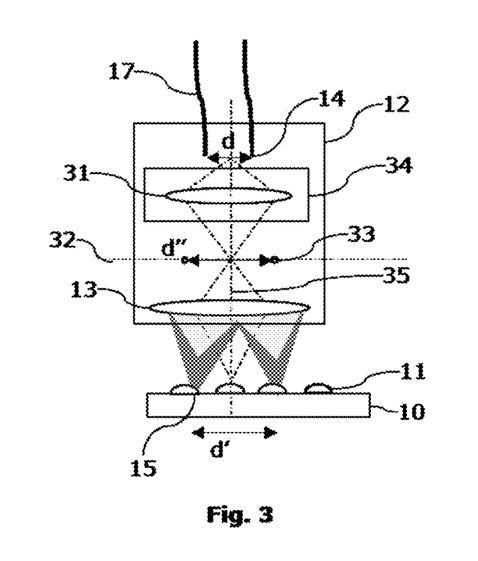
FIG. 3 illustrates a first mode of realization of measurement head with a magnifying lens.

FIG. 3 illustrates a mode of realization in which the magnifying lens 31 is arranged so as to image the collection apertures 14 in an intermediate conjugate focal plane 32 along the optical axis 35 with a first magnification factor G". If the collection apertures 14 are separated by a distance d in the plane perpendicular to the optical axis 35, their image 33 by the magnifying lens 31 is separated by a distance d"=G"d. The chromatic lens 13 is arranged so that the intermediate conjugate focal plane 32 is also a conjugate focal plane of the object plane with the measurement points 15. So, by assuming a second magnification factor G' for the chromatic lens 13 between the intermediate conjugate focal plane 32 and the plane of the measurement points 15, we obtain measurement points 15 separated by a distance d'=Gd, where G=G'G" is the magnification factor G corresponding to the global magnification factor of the combination of magnifying lens 31 and chromatic lens 13. Of course, in all modes of realization presented, the magnification factor G may correspond to a magnification, a reduction, or a unity magnification.

It is to be noted that the lateral size of the measurement points 15, corresponding to the lateral resolution of these measurement points 15, is also changed by the magnification factor, but the ratio between the separation distance d' and the lateral resolution at the measurement points 15 is preserved, which is the most important for the quality of the sampling.

Figure 4:
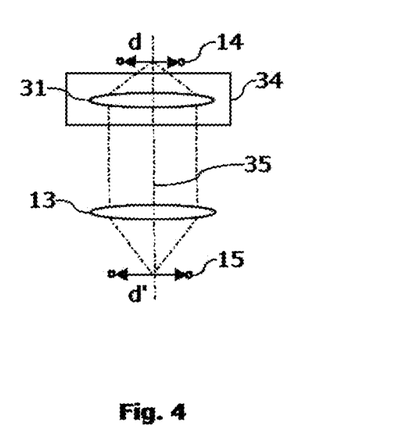
FIG. 4 illustrates a second mode of realization of measurement head with a magnifying lens.

FIG. 4 illustrates a mode of realization in which the magnifying lens 31 is arranged so that the collection apertures 14 are located in its entrance focal plane. In that case, the intermediate conjugate focal plane is at infinity and the magnification factor G is determined by the ratio of the focal lengths of the magnifying lens 31 and the chromatic lens 13. Of course the chromatic lens 13 is arranged to operate in such configuration.

Figure 5:
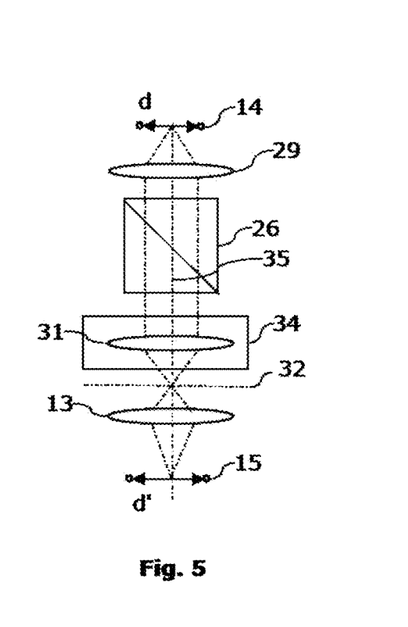
FIG. 5 illustrates a third mode of realization of measurement head with a magnifying lens.
Figure 6:
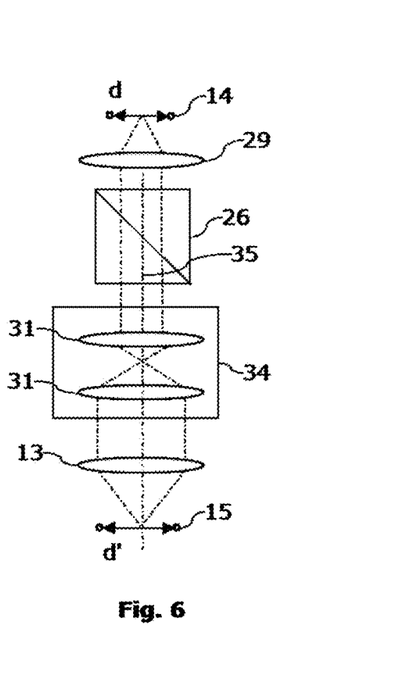
FIG. 6 illustrates a fourth mode of realization of measurement head with a magnifying lens.

FIG. 5 and FIG. 6 illustrate modes of realization of measurement head 12 with a magnifying lens 31 which are compatibles with the presence of a bulk beam splitter 26 as described in the modes of realizations of device illustrated in FIG. 2. Of course, these modes of realization may also be used with the modes of realization of device illustrated in FIG. 1, without beam splitter 26 but using a collimating lens 29 arranged so as to have the collection apertures 14 in its focal plane.

In case of use of a beam splitter 26, the magnifying lens 31 is placed between the beam splitter 26 and the chromatic lens 13, so as to have a same magnification factor G applied to the collection apertures 14 and the illumination apertures 28.

In the mode of realization of FIG. 5, the magnifying lens 31 is arranged (in combination with the collimating lens 29) so as to image the collection apertures 14 in an intermediate conjugate focal plane 32 with a first magnification factor G". In that case, the first magnification factor G" it determined by the ratio of the focal lengths of the magnifying lens 31 and the collimating lens 29. As previously, by assuming a second magnification factor G' for the chromatic lens 13 between the intermediate conjugate focal plane 32 and the plane of the measurement points 15, the (global) magnification factor G for the combination of magnifying lens 31 and chromatic lens 13 corresponds to G=G'G".

It is to be noted that, without beam splitter 26, the mode of realization of FIG. 5 is may be similar to the mode of realization of FIG. 4 if the collimating lens 29 is part of the magnifying lens assembly 31.

In the mode of realization of FIG. 6, the magnifying lens 31 comprises is an afocal lens arrangement, with for instance two lenses having their intermediate focal planes superposed. In that case, the intermediate conjugate focal plane (between the magnifying lens 31 and the chromatic lens 13) is at infinity. The magnification factor G may be determined as being the product G=G'G" of:
  a first magnification factor G' corresponding to the ratio of the focal lengths of the chromatic lens 13 and the collimating lens 29; and
  a second magnification factor G" corresponding to the ratio of the respective focal lengths of the lenses of the afocal lens pair comprised in the magnifying lens system 31.

It is to be noted that in the mode of realization of FIG. 6, the magnifying lens 31 has an infinite effective focal length, or in other words entrance and exit conjugate focal planes placed at infinity. That configuration has the advantage that the accuracy of the positioning of the magnifying lens 31 along the optical axis 35 is not critical for the performance.

As previously explained, a purpose of the magnifying lens 31 is to provide a capability to vary the magnification factor G of the optical set-up, either continuously or within a discrete set of values.

Several practical implementations are possible.

According to some modes of realization, the magnifying lens 31 comprises a zoom arrangement for varying continuously the magnification factor G over a range.

For instance, in the mode of realization of FIG. 6, the magnifying lens 31 may comprise an afocal zoom arrangement. According to a well-known configuration, such afocal arrangement may comprise two converging lenses of equal focal length, and a diverging lens with an absolute focal length less than half that of the converging lenses placed between the converging lenses. Such arrangement allows varying the magnification by moving the diverging lens and one of the converging lenses along the optical axis 35 in a particular non-linear relationship.

According to some modes of realization, the measurement head 12 comprises a mechanical mount 34 to change the magnifying lens 31.

The measurement head 12 may comprise for instance a turret 34 or a linear stage 34 holding several magnifying lens 31 and allowing to change the magnifying lens 31 inserted between the collection apertures 14 and the chromatic lens 13 by a translational or rotational movement. In that case, the different magnifying lenses 31 are arranged so that, once in place, the plane with the collection apertures 14 is conjugate of the object plane with the measurement points 15 by the whole optical system, comprising the magnifying lens 31 and the chromatic lens 13. If at least one of the conjugate focal planes of the magnifying lens 31 (that is the entrance plane towards the collection apertures 14 and/or the intermediate conjugate focal plane 32) is at a finite distance, which is the case for the modes of realization of FIG. 3, FIG. 4 or FIG. 5, the different magnifying lenses need to be positioned accurately along the optical axis 35. If both conjugate planes of the magnifying lens 31 are at infinite distance, which is the case for the mode of realization of FIG. 6, the requirements in terms of positioning along the optical axis 35 are relaxed.

The measurement head 12 may also comprise a turret or a linear stage holding several chromatic lenses 13 to be used with one fixed magnifying lens 31 or several interchangeable magnifying lenses 31.

The modes of realization of FIG. 1-FIG. 6 show devices with a few measurement channels 24 for sake of clarity. Of course, in practice a device of the invention may comprise much more measurement channels 24, in the order of hundred or more.

The spatial repartition of the collection apertures 14 in the measurement head 12 and the repartition of the intensity detectors 20 and the spectral detectors 21 among the optical measurement channels 24 may be of any kind, depending on the applications.

Figure 7:
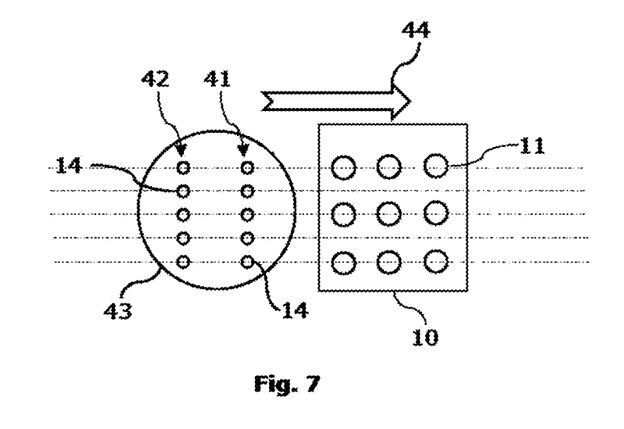
FIG. 7 illustrates a mode of realization of measurement head providing measurement points arranged in lines.

With reference to FIG. 7, we will now describe a mode of realization of device optimized for allowing high-speed inspection a surface of an object such as a wafer 10 with structures 11 such as bumps or micro-bumps 11.

The optical measurement channels 24 are provided with collection fibers 17 whose end forming the collection apertures 14 are arranged in two parallel rows positioned in a mounting piece 43 (for instance with grooved elements for accurately positioning the fiber ends).

A first row 41 comprises collection fibers 17 of measurement channels 24 connected to intensity detectors 20.

A second row 42 comprises collection fibers 17 of measurement channels 24 connected to spectral detectors 21.

The first row 41 and the second row 42 may have a same number of collection apertures 14 as illustrated in FIG. 4, or a different number, possibly with a different spacing.

The second row 42 may even have a single collection aperture 14 connected to a single spectral detector 21.

Of course, the spatial repartition of the measurement points 15 may be adjusted using a magnifying lens 31 as described in relation with FIG. 3-FIG. 6.

The main purpose of that specific arrangement, as it will be described later, is to provide a device which allows acquiring intensity information prior to axial distance information in a same scan.

Of course, other repartitions are possible. In particular, the collection apertures 14 may be arranged in one row 41. And these collection apertures 14 may optically be connected to:
  Only intensity detectors 20; or
  Only spectral detectors 21; or Intensity detectors 20 or, for one or several collection apertures located at the center of the row 41, spectral detectors 21.

Figure 8:
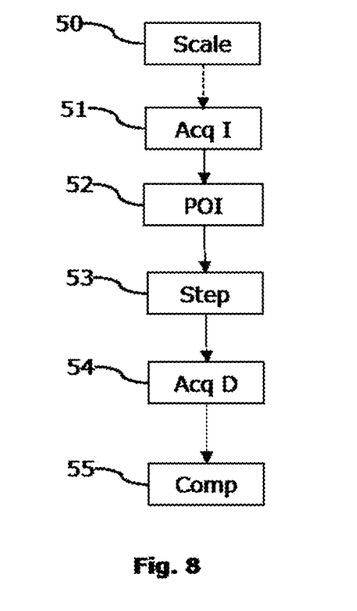
FIG. 8 illustrates a flow chart of the method of the invention.

With reference to FIG. 8, we will now describe a method for inspecting a surface of an object in 2D and 3D modes.

Generally speaking, the method of the invention comprises steps of:
- Acquiring an intensity information with several measurement channels 24 on several measurement points 15 at the surface of the objet 10 (step 51);
- Locating points of interests for axial distances measurements using said intensity information and possibly intensity information and/or axial distance information acquired during preceding steps (step 52);
- Positioning collection apertures 14 of at least one measurement channel 24 with a spectral detector 21 over a point of interest (step 53);
- Acquiring at least one axial distance information (step 54);
- repeating the process over the surface of the object 10 and computing the results (step 55).

The computation may comprise for instance at least one of the following: Building a height map, building an intensity map, locating structures in the X-Y plane, comparing height or in-plane dimensions of the structures with expected values, issuing pass/fail data.

Optionally, the method may comprise a step of adjusting the spatial repartition of the collection apertures 14 using a magnifying lens 31 (step 50).

That adjustment may be done using a-priori knowledge on the object, or using intensity information and/or axial distance information previously obtained. It may be done once at the beginning of the measurements or several times during the measurement process.

By using the set-up of the invention described in relation with FIG. 7, the method of the invention allows in particular doing a very high-speed inspection of a surface of a wafer 10 with structures 11 such as bumps or micro-bumps 11 arranged in a periodic fashion.

In a first step, the measurement head 12 and the wafer 10 are arranged so that the rows 41, 42 of collection apertures 14 are aligned with the structures 11. Optionally the magnification is adjusted with the magnifying lens 31 so that the distance between the measurement points 15 matches the spacing of the structures (with for instance one measurement point 15 on the top of the structure and one measurement point between two structures as illustrated on FIG. 7).

Then the measurement head is moved in a direction of displacement 44 preferably perpendicular to the rows 41, 42 of collection fibers. For each displacement step:
- An intensity information is acquired with the collection apertures 14 of the first row 41. It is combined with the previously acquired intensity information to build an intensity map;
- The intensity map is processed to locate the newly appearing structures 11 along in the X-Y plane. The next points of interest for axial distances measurements, corresponding for instance to summits of structures 11 are computed accordingly;
- If measurement points 15 corresponding to the collection apertures 14 of the second row 42 are positioned on previously identified points of interest, corresponding axial distance information is acquired. Newly acquired axial information is then combined with the previously acquired axial information to build a height map.

The process is repeated over the whole area of interest of the wafer and the data is computed for providing for instance at least one of the following: a height map, an intensity map, location of structures in the X-Y plane, comparison of height or in-plane dimensions of the structures with expected values, pass/fail data.

As previously, the magnification may be adjusted with the magnifying lens 31 using a-priori knowledge on the object or intensity information and/or axial distance information previously obtained once at the beginning of the measurements or several times during the measurement process between displacement steps.

The devices and the methods of the invention may advantageously be uses for several kind of applications. It may be used for instance for inspecting:
- an object 10 such as a wafer;
- an object 10 such as a wafer on carrier or glass carrier, or wafer elements such as dies on a carrier;
- an object 10 such as a wafer on frame, or wafer elements such as dies on a frame;

In particular, for the inspection of an object 10 made of several compound elements such as dies on carrier or frame, the method of the invention may comprise steps of:
- performing inspection steps as previously described with a high magnification leading to a coarse spatial resolution (and high speed) for locating on the surface of the carrier or frame, in the X-Y plane and possibly also in height Z, the compound elements (or dies); and
- performing inspection steps as previously described with a low magnification leading to fine spatial resolution for inspecting at least some of the compound elements (or dies), looking for instance on solder bumps on these compounds elements.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A confocal chromatic device for inspecting the surface of an object such as a wafer, comprising:
    a chromatic lens with an extended axial chromatism;
    a light source for illuminating the object through the chromatic lens with a plurality of optical wavelengths being focused at different axial distances;
    a plurality of optical measurement channels with collection apertures arranged for collecting the light reflected by the object through the chromatic lens at a plurality of measurement points; and
    a magnifying lens arranged for introducing a variable or changeable scaling factor between the spatial repartition of the collection apertures and the measurement points.

2. The device of claim 1, wherein the plurality of optical measurement channels comprises optical measurement channels with an intensity detector for measuring a total intensity of the collected light.

3. The device of claim 1, wherein the plurality of optical measurement channels comprises at least one optical measurement channel with a spectral detector for measuring a spectral information of the collected light and deducing an axial distance information.

4. The device of claim 1, which comprises a magnifying lens positioned between the collection apertures and the chromatic lens.

5. The device of claim 1, which comprises a magnifying lens and a chromatic lens arranged so that to provide an intermediate conjugate focal plane which is simultaneously:
- a conjugate focal plane of the plane with the collection apertures for a lens assembly comprising the magnifying lens; and
- a conjugate focal plane of the plane with the measurement points for a lens assembly comprising the chromatic lens.

6. The device of claim 5, wherein the intermediate conjugate focal plane is:
- at a finite distance; or
- at a finite distance and positioned between the magnifying lens and the chromatic lens.

7. The device of claim 6, wherein the intermediate conjugate focal plane is at infinite distance, corresponding to collimated beams.

8. The device of claim 1, further including a collimating lens positioned between the collection apertures and the magnifying lens.

9. The device of claim 7, further including a magnifying lens with an afocal lens arrangement.

10. The device of claim 1, which comprises a magnifying lens of a zoom type allowing introducing a variable magnification.

11. The device of claim 10, wherein the magnifying lens comprises:
- at least one lens movable and allowing varying a magnification;
- a lens arrangement allowing varying the magnification between the plane of the collection apertures and an intermediate conjugate focal plane at finite distance; and
- an afocal zoom arrangement allowing modifying the width of collimated beams, for operating with an intermediate conjugate focal plane at infinite distance.

12. The device of claim 1, which further comprises a mechanical mount allowing changing a magnifying lens.

13. The device of claim 12, wherein the mechanical mount comprises a turret or a linear stage.

14. The device of claim 1, further including collection apertures arranged along a line.

15. A method for inspecting the surface of an object such as a wafer comprising tridimensional structures, comprising:
- providing a chromatic lens with an extended axial chromatism;
- illuminating the object through the chromatic lens with a plurality of optical wavelengths being focused at different axial distances;
- collecting the light reflected by the object through the chromatic lens at a plurality of measurement points using a plurality of optical measurement channels with collection apertures; and
- changing optically a scaling factor between a spatial repartition of the collection apertures and a spatial repartition of the measurement points.

16. The method of claim 15, further comprising at least one of the following steps:
- measuring a total intensity of the light collected by at least one of the optical measurement channels for obtaining an intensity information; and
- measuring a spectral information of the light collected by at least one of the optical measurements channels for obtaining an axial distance information.

17. The method of claim 15, further comprising at least one of the following steps:
- adjusting a spatial repartition of the measurement points taking into account a spatial repartition of structures on the object; and
- adjusting a spacing of measurements points as to substantially match a spacing of structures on the object.

18. The method of claim 15, which is implemented for inspecting bump structures on a wafer.

* * * * *